United States Patent [19]

della Valle

[11] 4,349,566

[45] Sep. 14, 1982

[54] TREATMENT OF ARRHYTHMIA WITH 8-CHLORO- OR 8-BROMOCOUMARIN DERIVATIVES

[75] Inventor: Francesco della Valle, Padua, Italy

[73] Assignee: Fidia S.p.A., Abano Terme, Italy

[21] Appl. No.: 185,893

[22] Filed: Sep. 10, 1980

Related U.S. Application Data

[63] Continuation-in-part of Ser. No. 101,001, Dec. 6, 1979, abandoned.

[30] Foreign Application Priority Data

Dec. 19, 1978 [IT] Italy ............................... 30991 A/78

[51] Int. Cl.³ ............................................ A61K 31/37
[52] U.S. Cl. ................................................... 424/281
[58] Field of Search ......................................... 424/281

[56] References Cited

U.S. PATENT DOCUMENTS 3,282,938 11/1966 Ritter et al. ........................ 424/281

*Primary Examiner*—Frederick E. Waddell
*Attorney, Agent, or Firm*—Birch, Stewart, Kolasch and Birch

[57] ABSTRACT

A method of treating arrhythmia in mammals which comprises administering 8-chloro- or 8-bromo-3-($\beta$-diethylaminoethyl)-4-methyl-7-ethoxycarbonylmethoxycoumarin (or a pharmaceutically acceptable salt thereof) thereto. When formulated in conventional pharmaceutical preparations, the active ingredient may be administered orally or endovenously.

6 Claims, No Drawings

TREATMENT OF ARRHYTHMIA WITH 8-CHLORO- OR 8-BROMOCOUMARIN DERIVATIVES

BACKGROUND OF THE INVENTION

Cross-Reference to Related Application

This application is a continuation-in-part of copending application Ser. No. 101,001, filed on Dec. 6, 1979, now abandoned.

FIELD OF THE INVENTION

The present invention relates to a new therapeutic application of 8-chloro- or 8-bromo-3-($\beta$-diethylaminoethyl)-4-methyl-7-ethoxycarbonylmethoxycoumarin, of the formula:

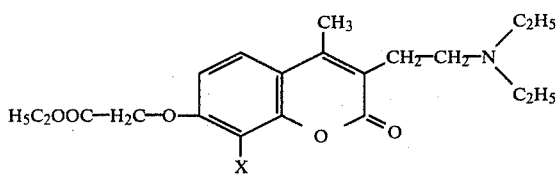

wherein X is a chlorine or bromine atom. These compounds, or pharmaceutically acceptable salts thereof, were obtained for the first time in the pure state, by means of highly selective processes developed by the present applicant.

As is the case with products that have more than one therapeutic activity, it has been discovered that 8-chloro- or 8-bromo-3($\beta$-diethylaminoethyl)-4-methyl-7-ethoxycarbonylmethoxycoumarin possesses, in addition to its known coronary vasodilating activity, also a good antiarrhythmic activity.

These properties have particularly become notable because of the selectivity of the method of preparation which permits halogenation at a single and predetermined position on the coumarin molecule, thus yielding a product free of impurities. Specifically, these compounds contain a chloro or bromo atom at the 8-position of the molecule.

To better illustrate the antiarrhythmic activity of said compounds, there are set forth by way of example a description of some experiments carried out, relating to two types of arrhythmia:
(1) that induced by aconitine, and
(2) that induced by adrenergic stimulation.

Proof of utility under conditions of ventricular arrhythmia in mammals

The following are the experimental conditions and methods which were used for measuring the antiarrhythmic activity.

(a) Arrhythmia induced with Aconitine

The experiments were carried out on male rats of the C. D. Sprague Dawley race of the Charles River having a weight between approximately 180 and 200 g.

The experimental arrhythmia was induced in the animal by means of aconitine, a substance which is known in the literature to produce ventricular extrasystoles and ventricular tachcyardia up to fibrillation (K. Peperand et al., Pfluger Arch., 296, 328–336, 1974).

The method used is described in the work of N. K. Dadkar et al, published in Arch. Int. Pharmadgyn., 212, 297–301, 1974. During each test, two rats in series (1 control and 1 treated) were immobilized on the operating table for the recording of the ECG by means of a Hewlett Packard polygraph with recording channels 8811A.

The 8-chlorocoumarin derivative was administered endovenously as an aqueous solution 10 minutes before the beginning of the slow infusion, into the vein of the tail, of the aconitine in a physiological solution (Fluka A. G.) at the concentration of 1.7 g/ml and at the rate of 0.15 ml/min by means of an infusion pump. The time of the outbreak of the extrasystoles, was then recorded, which is an indication of the resulting arrhythmia, both in the animals treated with the test compounds and in the control animals treated only with aconitine.

The antiarrhythmic activity of the test compounds was expressed as the latent time from the appearance of the extrasystoles and then as the dose of aconitine administered.

The 8-chlorocoumarin derivative was additionally compared with a pharmaceutical product having a known antiarrhythmic activity, and used in therapy, such as procainamide (Burnestein C. L., Anesthesiol., 10, 133, 1949) which was administered under the same conditions as the compound being tested.

The results are shown in Table I.

TABLE I

| | Antiarrhythmic Activity Arrhythmia induced by aconitine | | | |
|---|---|---|---|---|
| Substance | Dosage mg/kg i.v. | mcg of aconitine necessary to cause arrhythmia | % of protection | Data from |
| (1) None | — | 15.8 | | our experimental data — Ex. 8 |
| (2) Procainamide | 10 | 17.2 | 9% | our experimental |
| | 20 | 20.2 | 27% | data — Ex. 8 |
| (3) 8-chloro-3-($\beta$-diethylaminoethyl)-4-methyl-7-ethoxycarbonylmethoxycoumarin hydrochloride | 3 | 19.6 | 24% | our experimental |
| | 6 | 21.8 | 38% | data — Ex. 8 |

Similar results were obtained with the use of the 8-bromocoumarin derivative.

(b) Arrhythmia induced by adrenergic stimulation

The experiments were conducted on cats having a weight of about 2.50–3.00 kg.

The test animals were anaesthesized by means of an i.p. injection of a mixture of urethane-chloralol (250 mg/kg of urethane and 50 mg/kg of chloralol) and maintained under anaesthesia with chloralol (80 mg/kg) in case the need arose. Cannules were then inserted in the test animals for artificial respiration.

The animals were operated on for the insertion of two cannules in the right femoral vein and in the left femoral artery, necessary respectively for the injection of the test product and of the adrenalin and for the detection of the arterial pressure.

The recording of the pressure was necessary to evaluate the individual sensitivity to the adrenalin.

The arrhythmia was then induced by an endovenous injection of adrenalin, which was administered in physiological solution at the minimum dosage necessary to cause extrasystoles. The doses of adrenalin used varied from a range of 5 to 10 g/kg.

The appearance of extrasystoles was detected, as in the preceding case, with a Hewlett Packard 3960 recorder, connected to a 4588 optical recorder.

The test compound was administered 10 minutes after the adrenalin injection, after which there was ascertained the sensitivity of the test animal to the adrenalin itself.

The antiarrhythmic activity was evaluated on the basis of the total number of extrasystoles which were detected.

The method of induction of the arrhythmia is described by Corazza et al, Arch. Sci. Biol., 45 (2), 183-194, 1961.

The results are summarized in Table II which follows:

TABLE II

| | Antiarrhythmia activity Adrenalin-induced arrhythmia: | | | |
|---|---|---|---|---|
| Substance | Dosage mg/kg i.v. | Total number of extrasystoles | % of protection | Data from |
| (1) None | — | 12.16 | — | our experimental data — Ex. 8 |
| (2) Procainamide | 30 | 1.83 | 66.37% | our experimental data — Ex. 8 |
| (3) 8-chloro-3-($\beta$-diethyl-aminoethyl)-4-methyl-7-ethoxycarbonyl-methoxy-coumarin hydrochloride | 6 | 2.25 | 51.82% | our experimental data — Ex. 8 |

Again, the use of the 8-bromocoumarin derivative in lieu of the 8-chlorocoumarin derivative shown in Table II, gave similar results.

As is evident from these results, the compounds disclosed herein have an antiarrhythmic activity which, when compared with procainamide, shows higher precentage results of protection, even with the utilization of lower dosages thereof.

The 8-chloro- and 8-bromocoumarin derivatives employed in the present invention for the treatment of arrhythmia in mammals, as well as the pharmaceutically acceptable salts thereof such as the hydrochloride salt, can be therapeutically utilized orally or by injection. These compounds can be administered orally in different types of known preparations such as in the form of dragees, tablets or gelatin capsules as well as in other known forms and can be formulated in a manner well known to pharmaceutical chemists utilizing standard pharmaceutical excipients, carriers or diluents such as water, vegetable oils, syrup, gum arabic, gelatin, methylcellulose, polyglycols and others which may optionally be mixed with emulsifying agents. The compounds utilized in the present invention and the pharmaceutically acceptable salts thereof such as the hydrochloride salt may be injected intramuscularly or endovenously (intravenously) in the form of an injectable solution. The pharmaceutical preparations can be liquid or dried, for example lyophilized preparations, using suitable excipients or diluents which are well known to pharmaceutical chemists. Useful oral dosages for humans or animals are in the range of about 50–400 mg of active ingredient daily. Useful injection doses for said mammals are in the range of about 20–100 mg daily for intramuscular or intravenous injection.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method of treating arrhythmia in mammals which comprises administering thereto an effective antiarrhythmic amount of a compound having the formula:

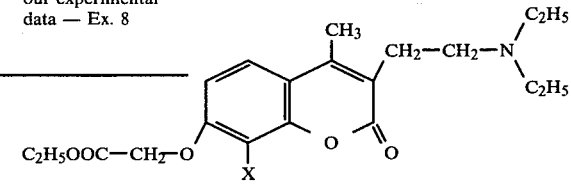

wherein X is chlorine or bromine, or a pharmaceutically acceptable salt thereof.

2. The method according to claim 1, wherein said compound is administered to a human or animal in an amount of about 50 to 400 mg. daily.

3. The method according to claim 1, wherein said compound is administered intramuscularly or endovenously to a human or animal in an amount of about 20 to 100 mg. daily.

4. The method according to claim 1, wherein said salt is the hydrochloride salt.

5. The method according to claim 1, wherein said compound is 8-chloro-3-($\beta$-diethylaminoethyl)-4-methyl-7-ethoxycarbonylmethoxycoumarin.

6. The method according to claim 1, wherein said compound is 8-bromo-3-($\beta$-diethylaminoethyl)-4-methyl-7-ethoxycarbonylmethoxycoumarin.

* * * * *